US008764740B2

(12) United States Patent
Watson (10) Patent No.: US 8,764,740 B2
(45) Date of Patent: Jul. 1, 2014

(54) SYSTEMS APPARATUS AND METHODS FOR DISTRIBUTING COOLANT WITHIN A CRYO-ABLATION DEVICE

(75) Inventor: James R. Watson, Santa Rosa, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 793 days.

(21) Appl. No.: 12/727,134

(22) Filed: Mar. 18, 2010

(65) Prior Publication Data

US 2010/0241112 A1 Sep. 23, 2010

Related U.S. Application Data

(60) Provisional application No. 61/162,443, filed on Mar. 23, 2009.

(51) Int. Cl.
 *A61B 18/02* (2006.01)
(52) U.S. Cl.
 USPC ............................... 606/21; 606/22; 606/23
(58) Field of Classification Search
 USPC ................................ 606/21–26; 607/96–105
 See application file for complete search history.

(56) References Cited

U.S. PATENT DOCUMENTS

| 5,261,879 | A |  | 11/1993 | Brill |
| 5,342,301 | A |  | 8/1994 | Saab |
| 6,355,029 | B1 |  | 3/2002 | Joye et al. |
| 6,468,297 | B1 |  | 10/2002 | Williams et al. |
| 6,821,275 | B2 | * | 11/2004 | Truckai et al. ............... 606/41 |
| 7,081,112 | B2 |  | 7/2006 | Joye et al. |
| 7,101,368 | B2 |  | 9/2006 | Lafontaine |
| 2002/0045892 | A1 |  | 4/2002 | Kramer |
| 2002/0077624 | A1 | * | 6/2002 | Lehmann et al. ............. 606/21 |
| 2003/0060762 | A1 | * | 3/2003 | Zvuloni et al. ............. 604/113 |
| 2006/0084962 | A1 |  | 4/2006 | Joye et al. |
| 2006/0100495 | A1 |  | 5/2006 | Santoianni et al. |
| 2008/0312644 | A1 |  | 12/2008 | Fourkas et al. |
| 2009/0234345 | A1 | * | 9/2009 | Hon ............................. 606/21 |

FOREIGN PATENT DOCUMENTS

WO 0207625 A2 1/2002

* cited by examiner

*Primary Examiner* — Michael Peffley
*Assistant Examiner* — Khadijeh Vahdat
(74) *Attorney, Agent, or Firm* — Seager, Tufte & Wickhem, LLC (57) ABSTRACT

Systems, apparatus and methods for dispersing a coolant along different portions of a supply tube of a cryo-ablation device which may be in the form of a linear ablation device or catheter probe or a balloon catheter. A supply tube includes multiple tubes that are in fluid communication with an inner space of a transmissive region or an inner space of an inflatable balloon. The tubes are coaxially arranged and extend to different lengths or to different locations such that the coolant is dispersed from different tubes at different axial locations. Annular apertures are defined by pairs of tubes and have different sizes. The tubes and arrangement thereof are structured to provide uniform or substantially uniform coolant distribution to provide uniform or substantially uniform cryo-ablation of surrounding tissue.

18 Claims, 13 Drawing Sheets

FIG. 13

# SYSTEMS APPARATUS AND METHODS FOR DISTRIBUTING COOLANT WITHIN A CRYO-ABLATION DEVICE

RELATED APPLICATION DATA

The present application claims the benefit under 35 U.S.C. §119 to U.S. provisional patent application Ser. No. 61/162,443, filed Mar. 23, 2009. The foregoing application is hereby incorporated by reference into the present application in its entirety.

FIELD OF THE INVENTION

The present inventions relate to cryo-ablation devices and related cryo-ablation methods.

BACKGROUND

Cardiac arrhythmias are a significant health problem, and atrial fibrillation is a common type of cardiac arrhythmia. Atrial fibrillation is an irregular heart rhythm that originates within the atria or the upper two chambers of the heart. The pulmonary veins, in particular, can be sources of disruptive electrical impulses that cause atrial fibrillation.

Medication is one known manner of treating atrial fibrillation and is intended to maintain a normal sinus rate and/or decrease ventricular response rates. It is also known to implant devices such as atrial pacemakers to treat atrial fibrillation. Other known methods and devices have been developed for creating therapeutic lesions in myocardial tissue, e.g., by use of minimally-invasive surgical methods, to block unwanted electrical impulses that are believed to be a source of atrial fibrillation. In this context, ablation has come to mean the deactivation, or removal of function, rather than the actual removal of tissue. A number of energy sources may be used for creating these "blocking" lesions that are preferably transmural and extend across the entire heart wall.

Formation of lesions may be performed using both endocardial and epicardial devices and techniques. Endocardial procedures are performed from within the heart. Since the endocardium primarily controls myocardial functions, there are inherent advantages to generating lesions by applying an energy source to endocardial surfaces. One known manner of applying energy for this purpose is utilizing radio frequency (RF) catheters. Certain known endocardial ablation devices include expandable balloons, which are inflated with a coolant such as nitrous oxide. Examples of known lesion formation devices, including cryogenic balloon devices for use in endocardial ablation, and their operation, are described in U.S. Patent Application Publication No. 20060084962, U.S. Pat. Nos. 5,261,879; 6,355,029; 6,468,297; 7,081,112 and 7,101,368, the contents of which are incorporated herein by reference.

While known cryo-ablation devices have been used effectively to some degree, they can be improved. In particular, releasing coolant through a central lumen of a supply tube may result in non-uniform coolant distribution within a cooling element or along a surface of a thermally transmissive region of a cyroablation device. More particularly, the concentration of coolant is highest at the outlet of the tube, and while this may be sufficient for purposes of cryo-ablation in a limited surrounding area, there are uneven mass flows and coolant pressures resulting from this configuration that may result in non-uniform distribution of coolant, which may result in non-uniform cooling and cryo-ablation which, in turn, may result in less effective and more time consuming cryo-ablation procedures.

One attempt to address these issues is to utilize a coolant supply tube that includes apertures that are formed through a wall of the supply tube. This allows coolant to be dispersed from multiple locations of a supply tube. However, such configurations may still result in non-uniform coolant distribution.

Figure 1:
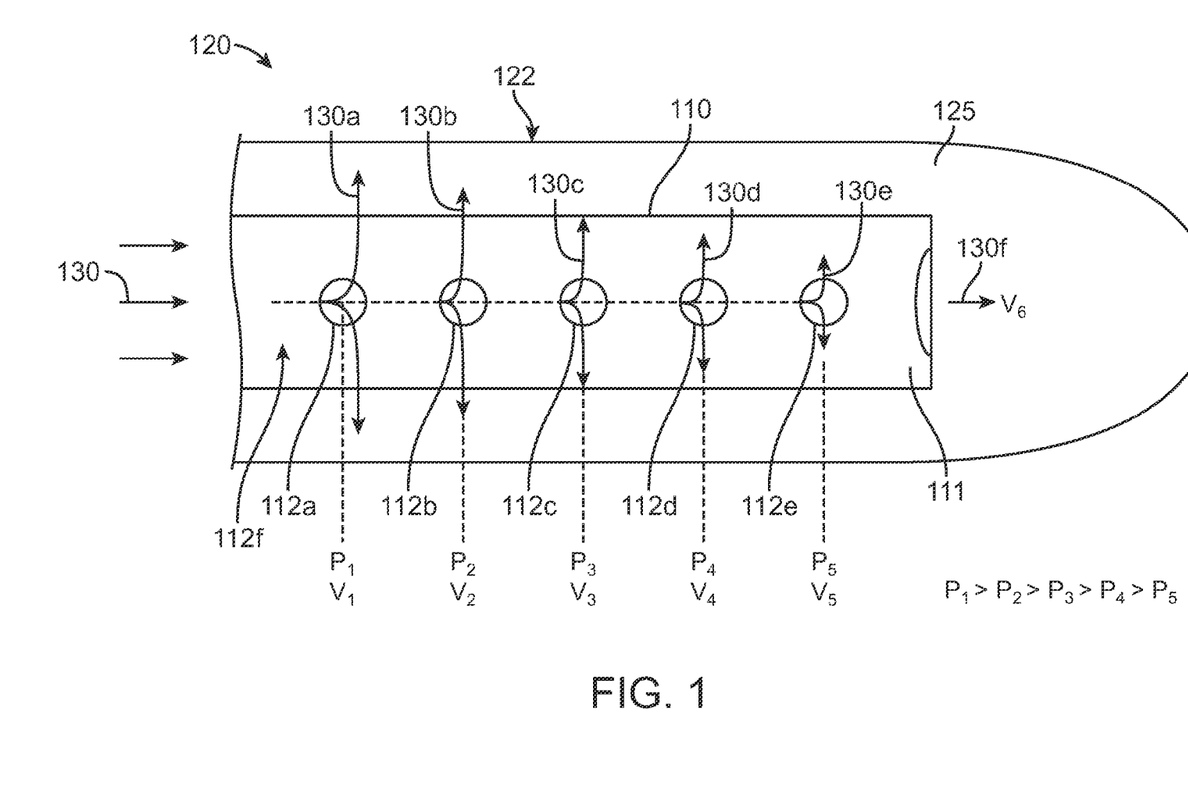
FIG. 1 illustrates a known supply tube having apertures resulting in uneven or non-uniform coolant flows and coolant pressures.

For example, referring to FIG. 1, a wall 111 of a coolant supply tube 110 that is positioned within a thermally transmissive region 122 of a body or element 125 of a cryo-ablation device 120 may include multiple apertures (five apertures 112a-e are shown) (generally aperture 112) and a central lumen 112f through which coolant 130 flows. The pressure of the coolant 130 that is dispersed through an aperture 112 is highest at the first or most proximal aperture 112a and decreases along the length of the supply tube 110 to a lowest pressure as coolant 130f exits the distal end of the supply tube 110. As a result, in the illustrated example, the pressure (P2) of coolant 130b dispersed through the second aperture 112b is less than the pressure (P1) of coolant 130a dispersed through the first aperture 112a, the pressure (P3) of coolant 130c dispersed through the third aperture 112c is less than the pressure (P2) of coolant 130b dispersed through the second aperture 112b the pressure (P4) of coolant 130d dispersed through the fourth aperture 112d is less than the pressure (P3) of coolant 130c dispersed through the third aperture 112c, the pressure (P5) of coolant 130e dispersed through the fifth aperture 112e is less than the pressure (P4) of coolant 130d dispersed through the fourth aperture 112d, and so on for more coolant 130 dispersed through more distal apertures. Uneven coolant pressure distribution may result in non-uniform fluid mass flows or coolant volumes (V1-V6) and corresponding uneven cooling and tissue ablation along the thermally transmissive region 122.

SUMMARY

According to one embodiment, an apparatus for dispersing a coolant within a cryo-ablation device comprises a tubular member having a plurality of coaxial tubes of different diameters. The coaxially arranged tubes extend to different respective lengths within the cryo-ablation device. The coaxial tubes define a corresponding plurality of annular spaces or apertures. Coolant can flow through the annular spaces and can be released from the plurality of tubes at different axial locations along the tubular member.

In accordance with another embodiment, an apparatus for dispersing a coolant within a cryo-ablation device comprises a first, tube, a second tube and a third tube. The second tube is coaxially disposed or positioned within the first tube and extends beyond a distal end of the first tube. The third tube is coaxially disposed or positioned within the second tube and extends beyond a distal end of the second tube. A first annular space is defined between an inner surface of the first tube and an outer surface of the second tube, and a second annular space is defined between an inner surface of the second tube and an outer surface of the third tube. The third tube defines a central lumen, and coolant that flows through the first and second annular spaces and the central lumen and be released from the first, second and third tubes at different axial locations within the cryo-ablation device.

In accordance with yet a further embodiment, an apparatus for dispersing a coolant within a cryo-ablation device comprises a first tube and a second tube that is coaxially disposed or positioned within the first tube and that extends beyond the first tube. An annular space is defined between an inner surface of the first tube and an outer surface of the second tube, and the second tube defines a central lumen such that coolant can flow through the annular space and the central lumen and be released from the first and second tubes at different axial locations within the cryo-ablation device.

In a further embodiment, a cryo-ablation device comprises a body and a tubular member for dispersing coolant within a thermally transmissive region of the body. The tubular member is positioned within the thermally transmissive region and comprises a plurality of coaxial tubes having different diameters and that extend to different lengths within the inner space to define a plurality of annular spaces. With this configuration, coolant can flow through the annular spaces and be released from the plurality of tubes at different axial locations along the tubular member and into the inner space of the thermally transmissive region.

A further embodiment is directed to a cryo-ablation device that comprises a body and a tubular member for dispersing the coolant within the thermally transmissive region of the body. The tubular member comprises three tubes, each of which are in fluid communication with an inner space of the thermally transmissive region. The second tube is coaxially disposed or positioned within the first tube and extends beyond a distal end of the first tube. The third tube is coaxially disposed or positioned within the second tube and extends beyond a distal end of the second tube. A first annular space is defined between an inner surface of the first tube and an outer surface of the second tube, a second annular space is defined between an inner surface of the second tube and an outer surface of the third tube, and the third tube defines a central lumen such that coolant can flow through the first and second annular spaces and the central lumen and be released from the tubes at different axial locations along the tubular member.

In accordance with another embodiment, a cryo-ablation device comprises a body and a tubular member for dispersing coolant within a thermally transmissive region of the body. The tubular member comprises a first tube and a second tube coaxially disposed within the first tube and extending beyond the first tube. An annular space is defined between an inner surface of the first tube and an outer surface of the second tube and the second tube defines a central lumen such that coolant can flow through the annular space and the central lumen and be dispersed from the first and second tubes at different axial locations along the tubular member.

Another embodiment is directed to a method of dispersing coolant within a thermally transmissive region of a cryo-ablation device. The method comprises supplying coolant to a tubular member within a body. The tubular member has a plurality of coaxial tubes having different diameters and extending to different lengths such that they define plurality of annular spaces. The method further comprises dispersing the coolant from the tubes through the annular spaces at different axial locations along the tubular member and into an inner space of the thermally transmissive region.

A further embodiment is directed to a method of dispersing coolant within a thermally transmissive region of a cryo-ablation device and includes supplying coolant to a tubular member within a body of the device. The tubular member comprises three tubes. A second tube is coaxially disposed or positioned within the first tube and extends beyond a distal end of the first tube, and a third tube coaxially disposed or positioned within the second tube and extends beyond a distal end of the second tube. A first annular space is defined between an inner surface of the first tube and an outer surface of the second tube. A second annular space is defined between an inner surface of the second tube and an outer surface of the third tube, and the third tube defines a central lumen. The method further comprises dispersing the coolant from the tubes through the annular spaces and the central lumen at different axial locations along the tubular member and into the inner space of the thermally transmissive region.

Another embodiment is directed to a method of dispersing coolant within a thermally transmissive region of a cryo-ablation device. The method comprises supplying coolant to a tubular member within a body of the cyroablation device. The tubular member comprises a first tube and a second tube coaxially disposed within the first tube and extending beyond the first tube. An annular space is defined between an inner surface of the first tube and an outer surface of the second tube and the second tube defines a central lumen. The method further comprises dispersing the coolant from the tubes through the annular space and the central lumen at different axial locations along the tubular member and into the inner space of the thermally transmissive region.

One or more apparatus embodiments and one or more method embodiments may involve or be utilized within a cryogenic balloon catheter rather than a non-inflatable or non-expandable cryo-ablation device or probe.

In one or more embodiments, coaxial tubes are arranged in a telescoping configuration, and a central tube defines a central lumen through which coolant, such as nitrous oxide, may also flow and be released or dispersed into an inner space of a transmissive region or into an inner space of an inflatable element of a catheter body. Tubes may be configured such that a quantity of coolant released at each axial location is approximately the same such that the coolant is uniformly or substantially uniformly distributed within the thermally transmissive region or inflatable element. The tubes may be arranged such that the coolant is released or dispersed at different axial locations that are substantially equidistant from each other.

In one or more embodiments, coaxially arranged tubes extend to different lengths such that the smallest cross-sectional area or diameter tube extends to the greatest length within a thermally transmissive region or inflatable element compared to other, larger cross-sectional area or diameter tubes. In one or more embodiments, the coaxially arranged tubes, which may be the same shape, e.g., cylindrical in shape, define annular spaces of different sizes or cross-sectional areas, which may become larger towards the distal end of a tubular member, and a central lumen defined by a central tube may have a larger area than an annular space defined by a pair of tubes.

BRIEF DESCRIPTION OF THE DRAWINGS

Referring now to the drawings in which like reference numbers represent corresponding parts throughout and in which.

DETAILED DESCRIPTION OF ILLUSTRATED EMBODIMENTS

Embodiments relate to cryo-ablation systems, apparatus and methods for dispersing a cryogen or coolant from a tubular member comprised of multiple individual supply tubes or supply tube segments or sections that extend to different lengths or to different locations within a thermally transmissive region of a cryo-ablation device. The cryo-ablation device may be a non-expandable or non-inflatable cryo-ablation device such as a probe or catheter or an inflatable or balloon cryo-ablation device. In one embodiment, the tubes are arranged in a coaxial manner. In another embodiment, the tubes are arranged in a non-coaxial manner.

With embodiments, a cryogenic fluid or coolant is distributed across a length of the supply tube and to various areas within the thermally transmissive region in a uniform or substantially uniform manner. This is accomplished using coolant flows through annular spaces defined between tubes and/or through a lumen defined by a single tube. In this manner, embodiments improve the effectiveness of cyroablation procedures by addressing issues of uneven or non-uniform coolant pressures or coolant flows and associated uneven or non-uniform cooling and cryo-ablation of tissue. Further aspects of embodiments are described with reference to FIGS. 2-13.

Figure 2:
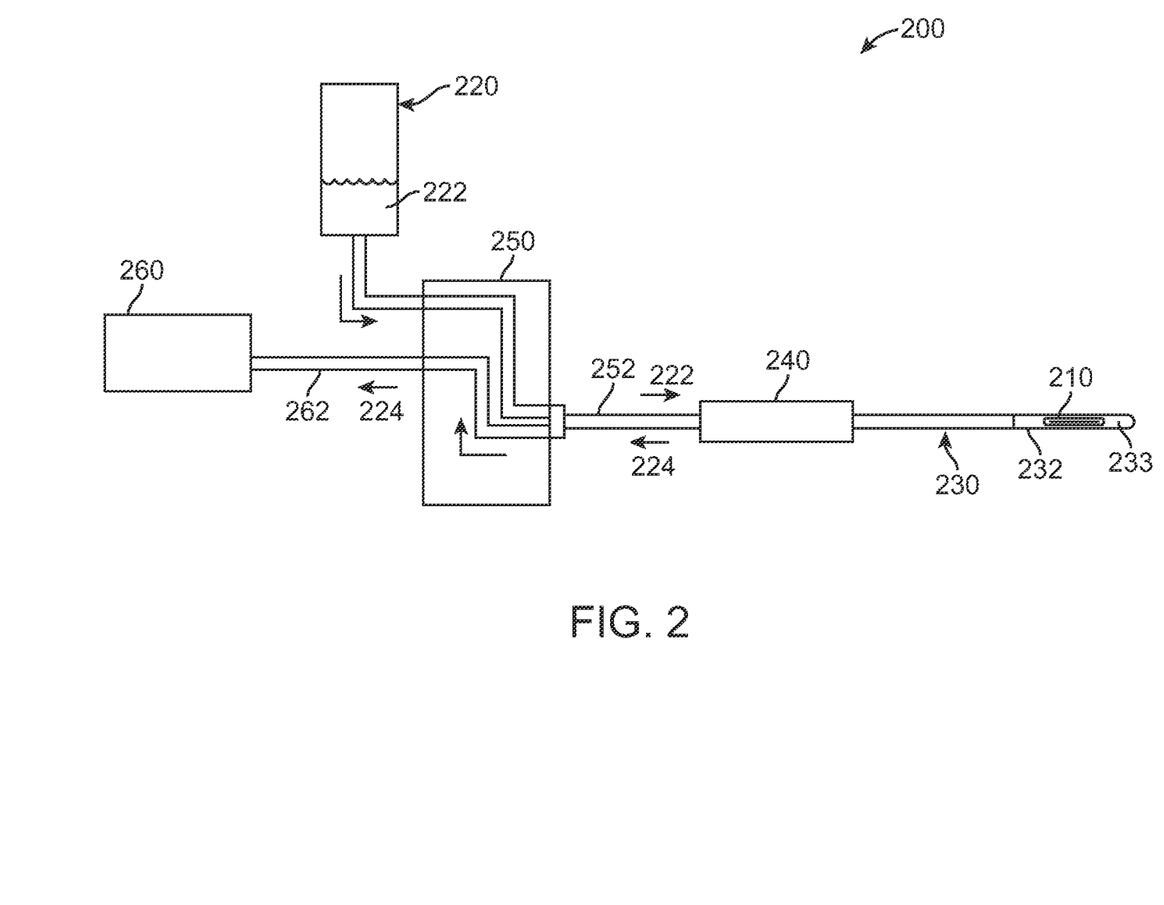
FIG. 2 schematically illustrates a cryo-ablation system and generally illustrates a tubular member constructed according to embodiments and having multiple coaxial tubes of different lengths for dispersing coolant in a thermally transmissive region of a catheter body.

FIG. 2 illustrates a cryo-ablation system 200 in which embodiments of a tubular member 210 having multiple individual supply tubes that extend to different lengths or to different locations may be implemented includes a container or source 220 of coolant, cryogenic fluid or refrigerant 222 (generally referred to as coolant 222). One example of a coolant 222 that may be utilized with embodiments is nitrous oxide. The coolant 222 may be a liquid, a gas or a mixture of thereof. Other coolants 222 that may be utilized include, but are not limited to, $CO_2$, Ar, $N_2$ and Freon. For ease of explanation, reference is made to a coolant 222 generally or nitrous oxide.

A flexible catheter or probe body, shaft or member 230 extends from a distal end of handle or interface 240 and is in fluid communication with a console or controller 250 via one or more supply tubes 252, which are used to deliver coolant 222 through the handle 240, through the flexible member 230, through the tubular member 210 constructed according to embodiments, and into an inner space 233 of a thermally transmissive region 232. Spent coolant 224 may be evacuated using a vacuum 260 and associated vacuum tubing 262.

In the illustrated embodiment, the thermally transmissive region 232 is a non-inflatable distal portion or tip of a probe body 230. The thermally transmissive region 232 may also be a different portion of the body 230 and may be various lengths. A tubular member 210 constructed according to embodiments is positioned within or extends at least partially within the inner space 233 of the thermally transmissive region 232 to disperse or spray coolant 222 within the inner space 233 to chill the thermally transmissive region 232 and cryogenically ablate surrounding tissue.

Figure 3:
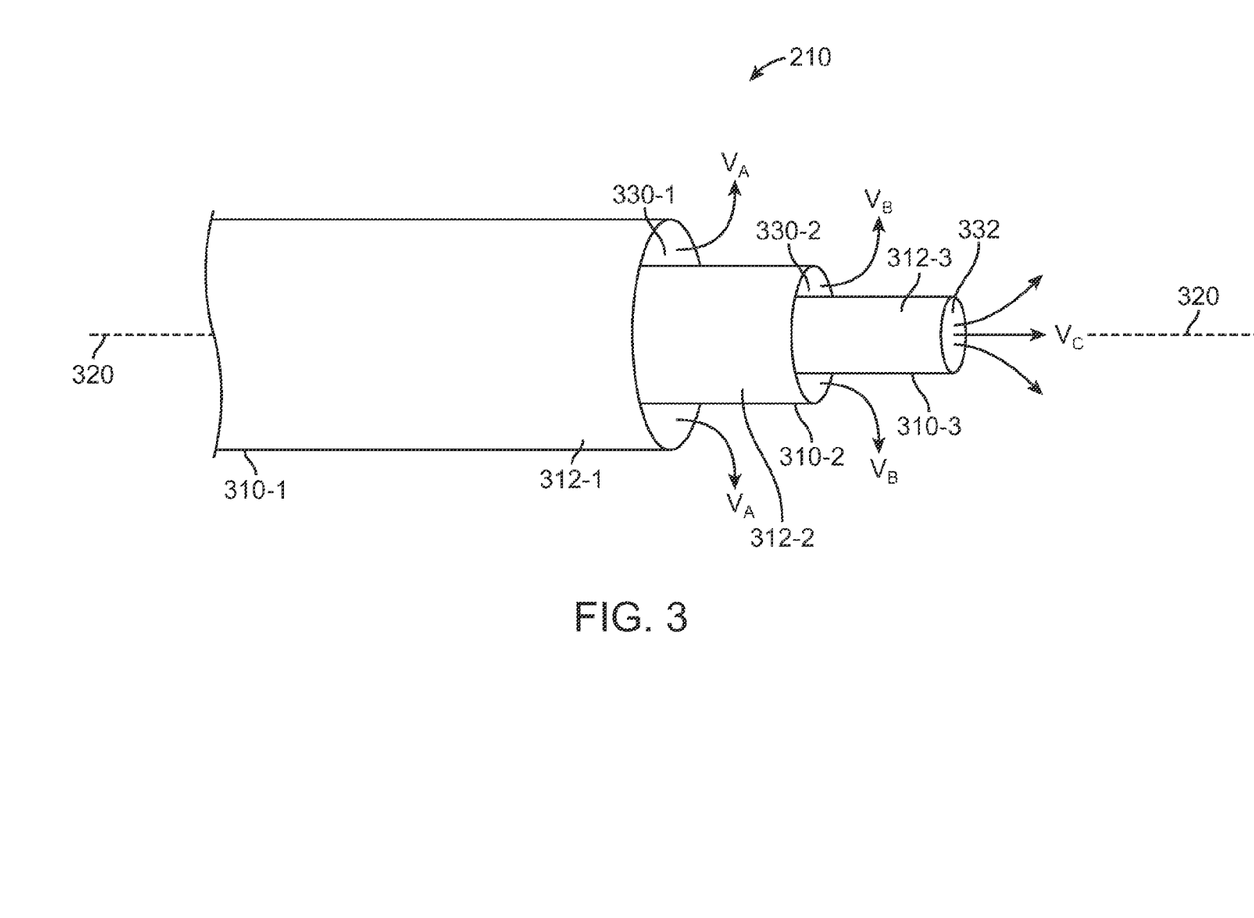
FIG. 3 illustrates a tubular member constructed according to one embodiment for dispersing coolant in a thermally transmissive region of a catheter body and having three coaxially arranged tubes that extend to different lengths and define a plurality of annular spaces and a central lumen from which cryogenic coolant can be released.

Referring to FIG. 3, a tubular member 210 constructed according to one embodiment includes a first tube 310-1, a second tube 310-2, and a third tube 310-3 (generally referred to as tubes 310). In the illustrated embodiment, each tube 310 is the same cylindrical shape, but in other embodiments, the tubes 310 may have different shapes. For ease of explanation and illustration, reference is made to a tube 310 having a cylindrical shape, but other shapes may be utilized. In the illustrated embodiment, all of the tubes 310 are different sizes, are coaxially arranged about a common axis 320, e.g., in a telescoping manner, and extend to different lengths or to different locations within the inner space 233 of a thermally transmissive region 232. More specifically, the third tube 310-3 is the smallest of the tubes 310 and is disposed within a lumen of the second tube 310-2, and the second tube 310-2 is smaller than and disposed within the lumen of the first tube 310-1. A distal end 312-3 of the third tube 310-3 extends beyond the distal end 312-2 of the second tube 310-2, which extends beyond the distal end 312-1 of the first tube 310-1. In this manner, a first annular space 330-1 is defined between an outer surface of the second tube 310-2 and an inner surface of the first tube 310-1, a second annular space 330-2 is defined between an outer surface of the third tube 310-3 and an inner surface of the second tube 310-2, and the smallest or inner tube 310-3 defines a central lumen 332.

Figure 4:
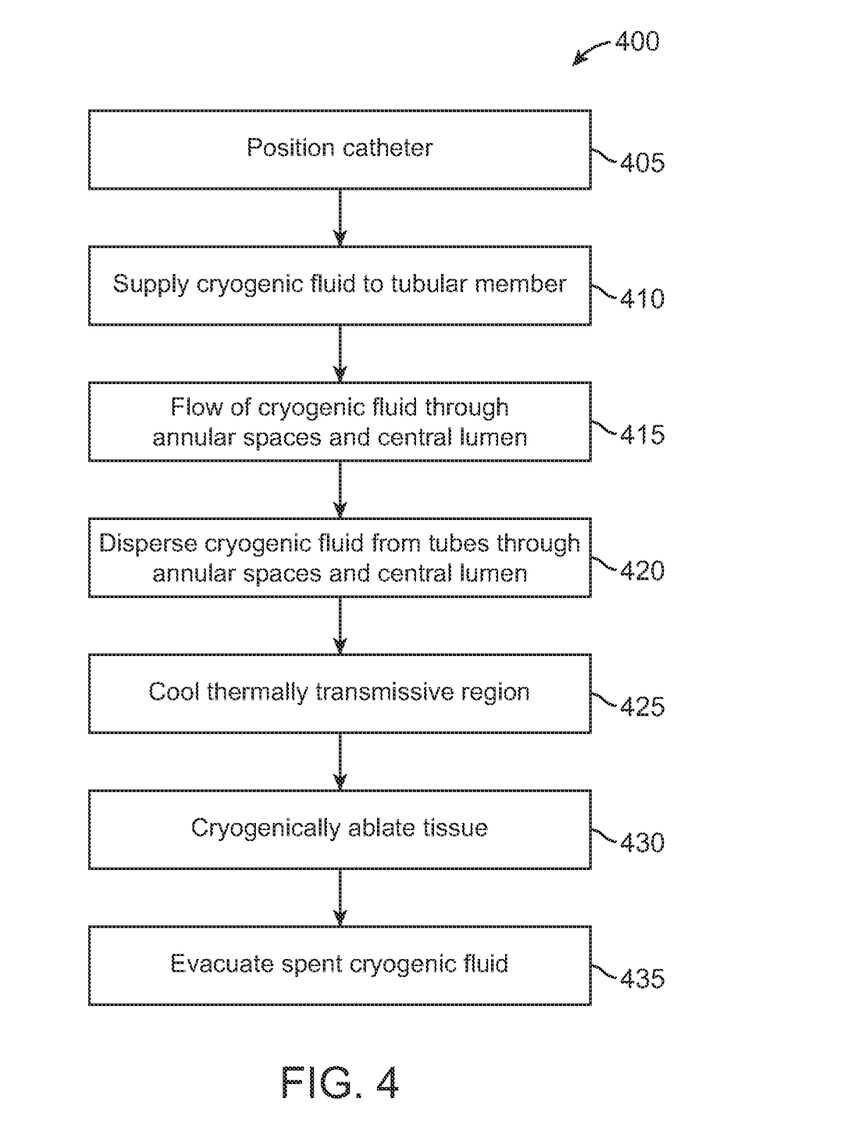
FIG. 4 is a flow diagram of a method of dispersing coolant within a thermally transmissive region of a catheter body utilizing a tubular member constructed according embodiments.

With further reference to FIG. 4, a method 400 for performing cryo-ablation with tubular member 210 embodiments (e.g., as shown in FIG. 3) includes, at stage 405, manipulating or positioning the cyroablation device 120 at a desired location within a patient. For example, a flexible body 230 may be advanced through vasculature and positioned within a heart of the patient, e.g., to treat atrial fibrillation, using a handle 123 or other component or control element such as a guide wire (not illustrated in FIG. 2) that extends through the catheter body 230.

At stage 410, one or more valves may be manipulated or controlled such that coolant 222 is released from the container 220 or allowed to flow through a console or interface 250 and associated connectors or tubes 252, through the handle 240 and catheter body 230, and to the tubular member 210 that is positioned within and in fluid communication with the inner space 233 of the thermally transmissive region 233. At stage 415, the coolant 222 flows through different sections of the tubular member 210.

Referring again to FIG. 3, in the illustrated embodiment, stage 415 involves coolant 222 flowing through the first and second annular spaces 330-1 and 330-2 and through the central lumen 332 of the tubular member 210. In the illustrated embodiment, the tubular member 210 includes coaxial tubes 310-1, 310-2 and 310-3 that define respective annular spaces 330-1 and 330-2 and a central lumen 332. The tubes 310 have different diameters, and the annular spaces 330 have different cross sectional areas. In one embodiment, the area of an annular space 330 increases from a proximal portion to a distal portion of the tubular member 210.

For example, the cross-sectional area of the first or more proximal annular space 330-1 is less than the cross-sectional area of the second or more distal annular space 330-2. With this configuration, more coolant 222 can flow through the second annular space 310-2 defined between the second and third tubes 310-2 and 310-3 compared to the first annular space 330-1 defined between the shorter first tube 310-1 and the second tube 310-2 to compensate for increased frictional forces resulting from coolant 222 flowing through a longer length of a smaller tube. Thus, with embodiments, the quantities or volumes (Va to Vc) of coolant 222 released from the tubes 310 at each axial location along the tubular member 210 may be approximately the same (Va~Vb~Vc) such that the coolant 222 is uniformly sprayed into and distributed within the inner space 233 of the thermally transmissive region 232. The tubes 310 and associated annular spaces 330 and/or central lumen 332 can be configured such that coolant 222 is released through the annular spaces 339 and/or central lumen 332 at different locations that are equidistant from each other. In other embodiments, the coolant 222 release locations may different depending on the configuration of the tubular member 210 and desired coolant 222 distribution.

In one embodiment, the tubes 310 can have an outer diameter of about 0.007" to about 0.25" (a range of diameters of the assembly of tubes), and the inner diameter of the smallest or inner tube may be greater than 0.003" such that frictional losses do not impede pumping of coolant 222. The distal end of a tube 310 may extend beyond a distal end of a more proximal tube 310 by about 0.004" to about 4". The cross-sectional area of an annular space 330 may vary depending on, for example, the number of tubes 310, the tube material and the wall thickness of a tube which may, for example, be about 0.001" to about 0.005", and desired flow rates. The cross-sectional area of the central lumen 332 may be larger than the annular spaces 330.

For example, the tube 310-1 can have an outer diameter of about 0.125", the tube 310-2 can have a diameter of about 0.060", and the tube 310-3 can have a diameter of about 0.020". The distal end of the tube 310-2 may extend beyond a distal end of the tube 310-1 by about 0.25", and the distal end of the tube 310-3 may extend beyond a distal end of the tube 310-2 by about 0.25". The area of the central lumen 332 defined by the inner or central tube may be less than the area of one or more apertures.

Referring again to FIG. 4, at stage 420, the coolant 222 flows through the annular spaces 330 and the central lumen 332 as discussed above and is released, dispersed or sprayed from the respective annular outlets 330 and/or central lumen 332 defined by the respective tubes 310 at different axial locations along the tubular member 210. According to one embodiment, the quantity of coolant 222 released at each axial location is approximately the same such that the coolant 222 can be uniformly or substantially uniformly distributed within the inner space 233 of the thermally transmissive region 232 to uniformly or substantially uniformly chill the thermally transmissive region 232 at stage 425, and cryogenically ablate tissue that is adjacent to or that surrounds the chilled thermally transmissive region 232 at stage 430. With embodiments, tissue ablation 430 is uniform or substantially uniform as a result of the uniform or substantially uniform distribution of coolant 222 within the thermally transmissive region 232. At stage 435, spent coolant 224 is evacuated from the body 125 through an exhaust path using associated vacuum tube 262 and vacuum source 260, which may be connected to or part of an open loop system, a closed loop system or a scavenging system.

Figure 5:
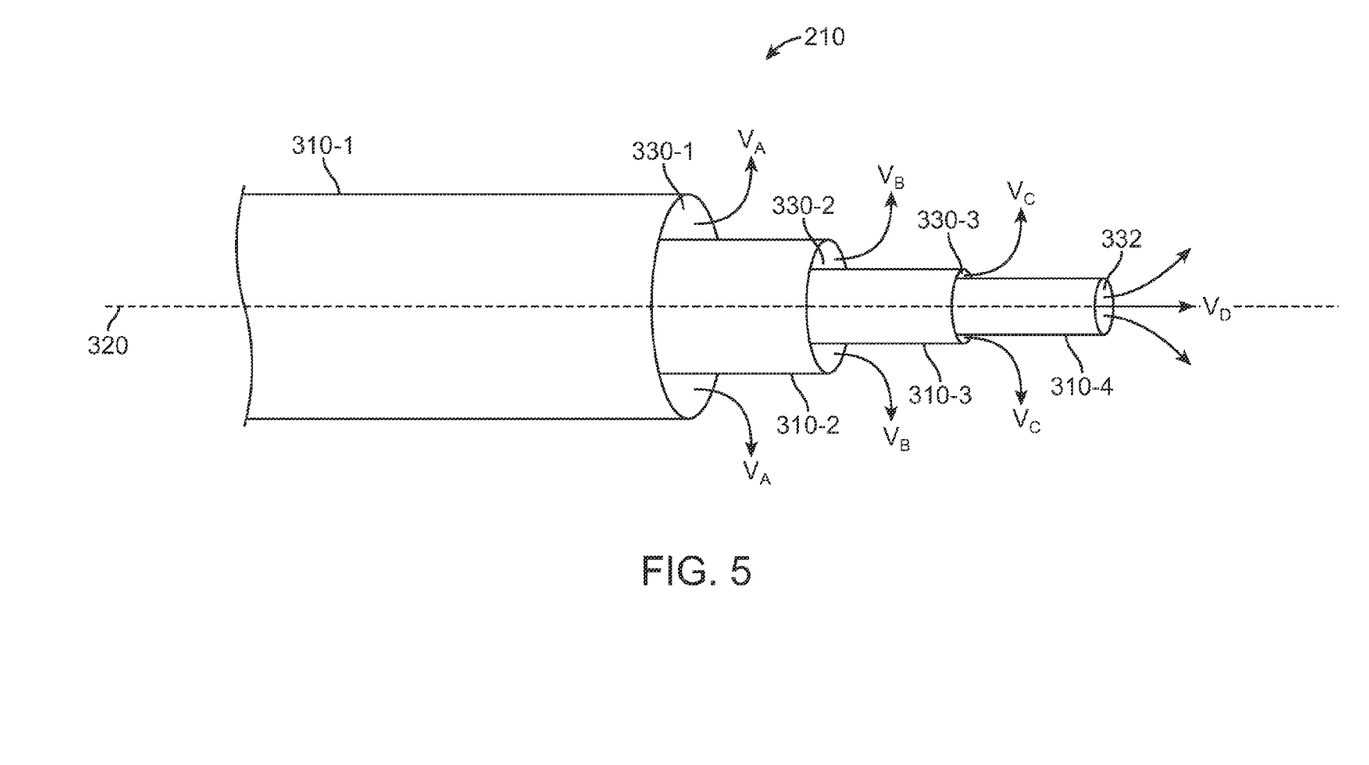
FIG. 5 illustrates a tubular member constructed according to another embodiment and that includes four coaxial tubes that extend to different lengths and define a plurality of annular spaces and a central lumen from which cryogenic fluid can be released
Figure 6:
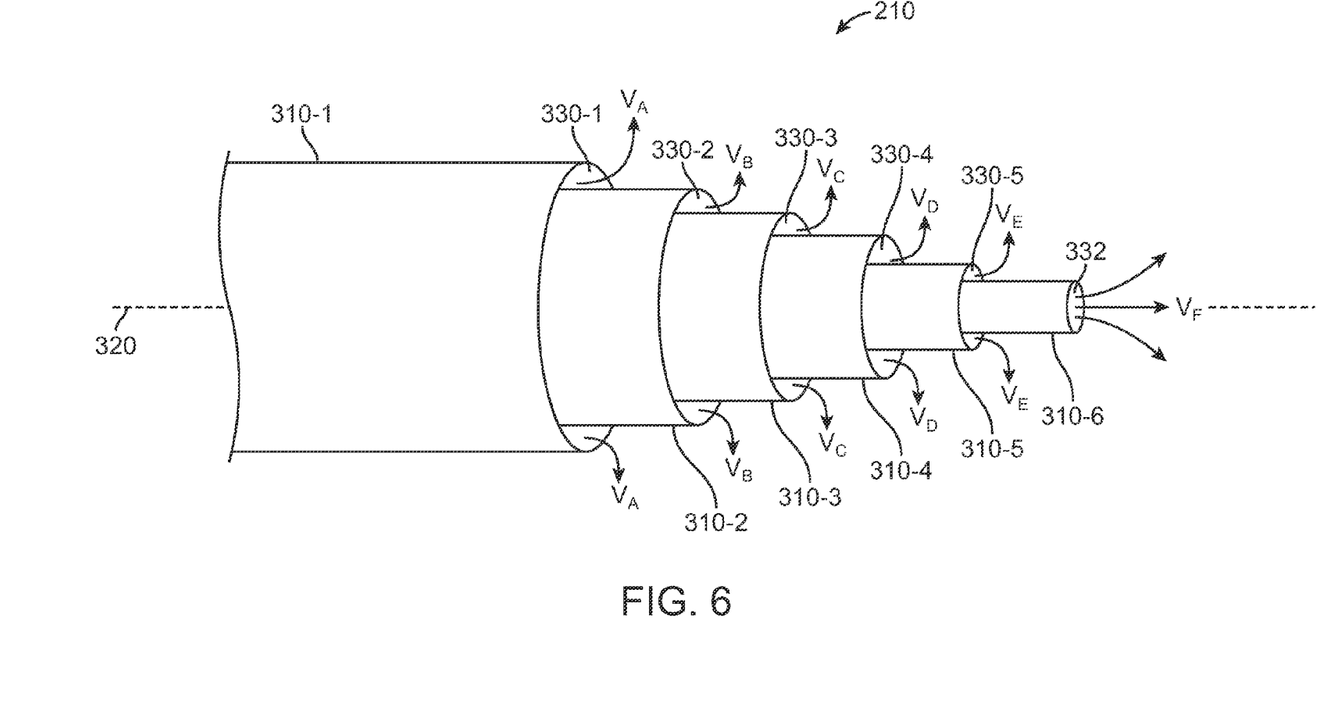
FIG. 6 illustrates a tubular member constructed according to another embodiment having six coaxial tubes that extend to different lengths and define a plurality of annular spaces and a central lumen from which coolant can be released.
Figure 7:
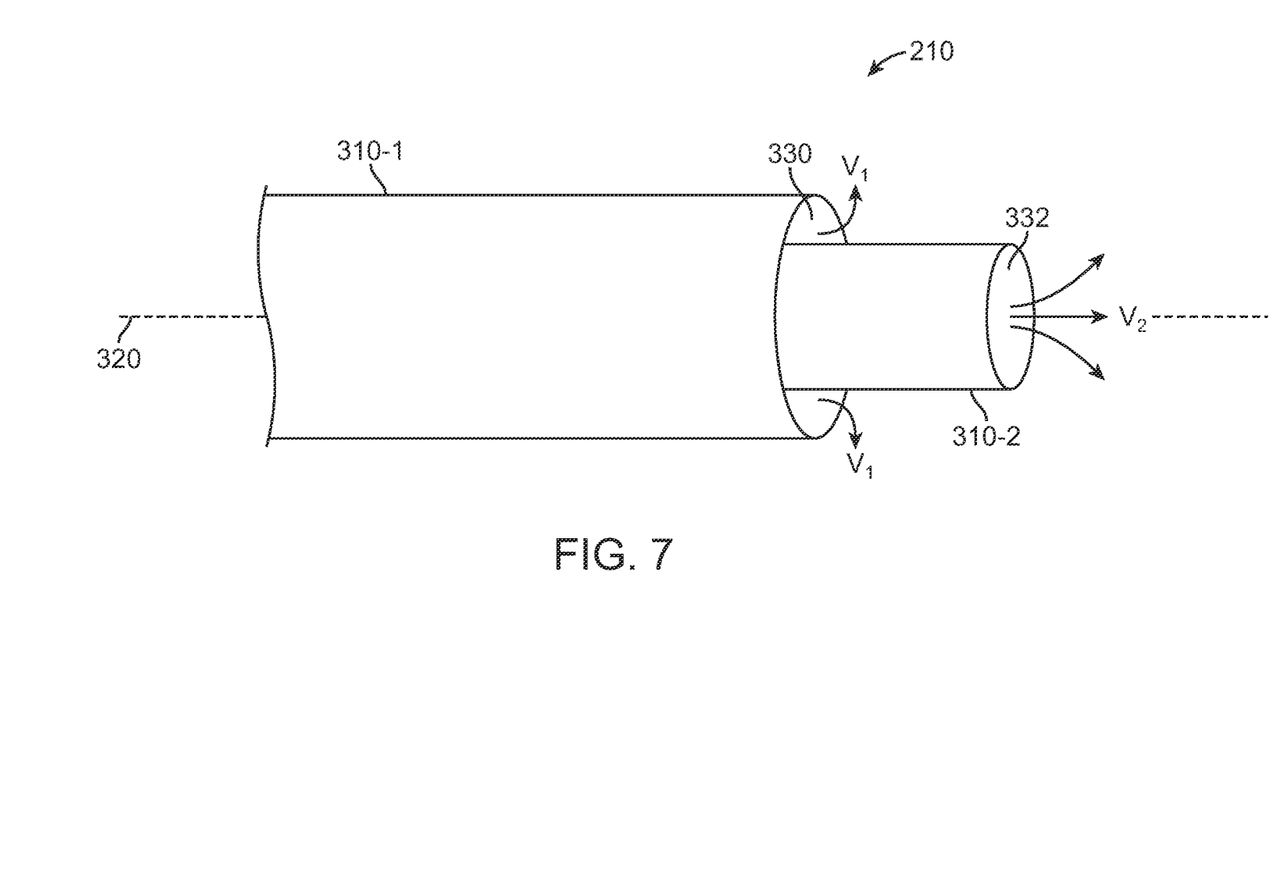
FIG. 7 illustrates a tubular member constructed according to another embodiment having two coaxial tubes that extend to different lengths and define an annular space and a central lumen from which a cryogenic coolant can be released.

Although FIGS. 3 and 4 illustrate and describe embodiments of a tubular member 210 having three coaxial tubes 310-1, 310-2 and 310-3 that extend to different lengths and define two annular spaces 330-1 and 330-2 and a central lumen 332, other embodiments may involve other numbers of tubes so arranged, e.g., as shown in FIGS. 5-7 that provide for uniform or substantially uniform coolant 222 distribution and cryo-ablation of tissue.

Referring to FIG. 5, another embodiment of a tubular member 210 includes four coaxially arranged tubes 310-1 to 310-4 that extend to different lengths or to different locations and define respective annular spaces 330-1 to 330-3 and a central lumen 232 through which coolant 222 may flow (Va-Vd). In another embodiment, referring to FIG. 6, a tubular member 210 includes six coaxially arranged tubes 310-1 to 310-6 that extend to different lengths that define respective annular spaces 330-1 to 330-5 and a central lumen 232 through which coolant 222 may flow (Va-Vf). In a further embodiment, referring to FIG. 7, a tubular member 210 includes two coaxially arranged tubes 310-1 and 310-2 that extend to different lengths that define an annular space 330 and a central lumen 232 through which coolant 222 may flow (Va-Vb). Thus, FIGS. 3-7 illustrate examples of how embodiments may be implemented, and a tubular member 210 may include different numbers of coaxially arranged tubes 310 that define different numbers of annular spaces 330 from which coolant 222 may be dispersed.

Figure 8:
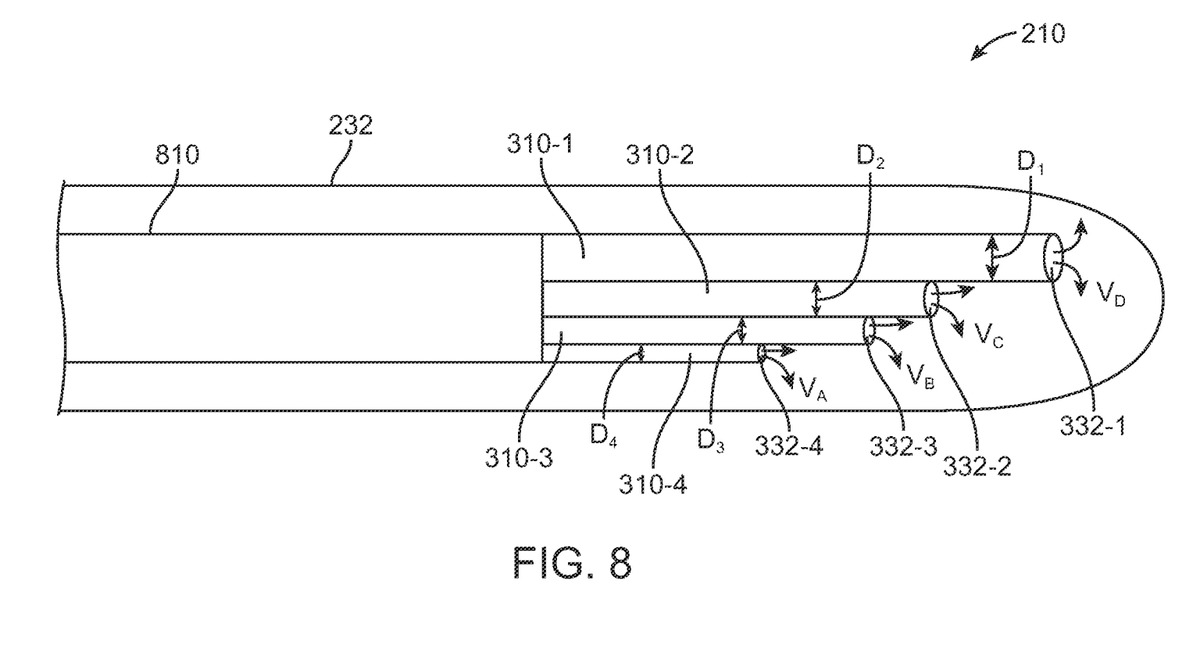
FIG. 8 illustrates another embodiment of a tubular member for dispersing coolant at different axial locations and having multiple tubes that are arranged in a non-coaxial manner and that extend to different lengths to disperse cryogenic coolant at different points along a length of the tubular member.

Referring to FIG. 8, according to another embodiment, a tubular member 210 includes a plurality of tubes, e.g., four tubes 310-1 to 310-4, having different diameters D1-D4. The tubes 310 may extend from a supply tube section or other tube or sheath component 810 and are arranged adjacent to each other. Each tube defines a lumen 332. In the illustrated embodiment, the tubes 310 are arranged in a manner similar to an arrangement of organ-like arrangement in which the smallest tube 310-1 terminates before the next largest tube 310-2, which terminates before the next larger tube 310-3, which terminates before the largest tube 310-4 such that the tubes 310-1 to 310-4 extend to different lengths within the inner space 233 of the thermally transmissive region 232. In this manner, a larger quantity of coolant 222 can flow through the larger tubes compared to the smaller tubes to compensate for increased frictional forces resulting from coolant 222 flowing through a longer length of a smaller tube, thereby resulting in the quantities or volumes (Va-Vd) of coolant 222 released from the tubes 310 at each axial location along the tubular member 210 being approximately the same (Va~Vb~Vc~Vd) such that the coolant 222 is uniformly sprayed into and distributed within the inner space 233 of the thermally transmissive region 232.

Figure 9:
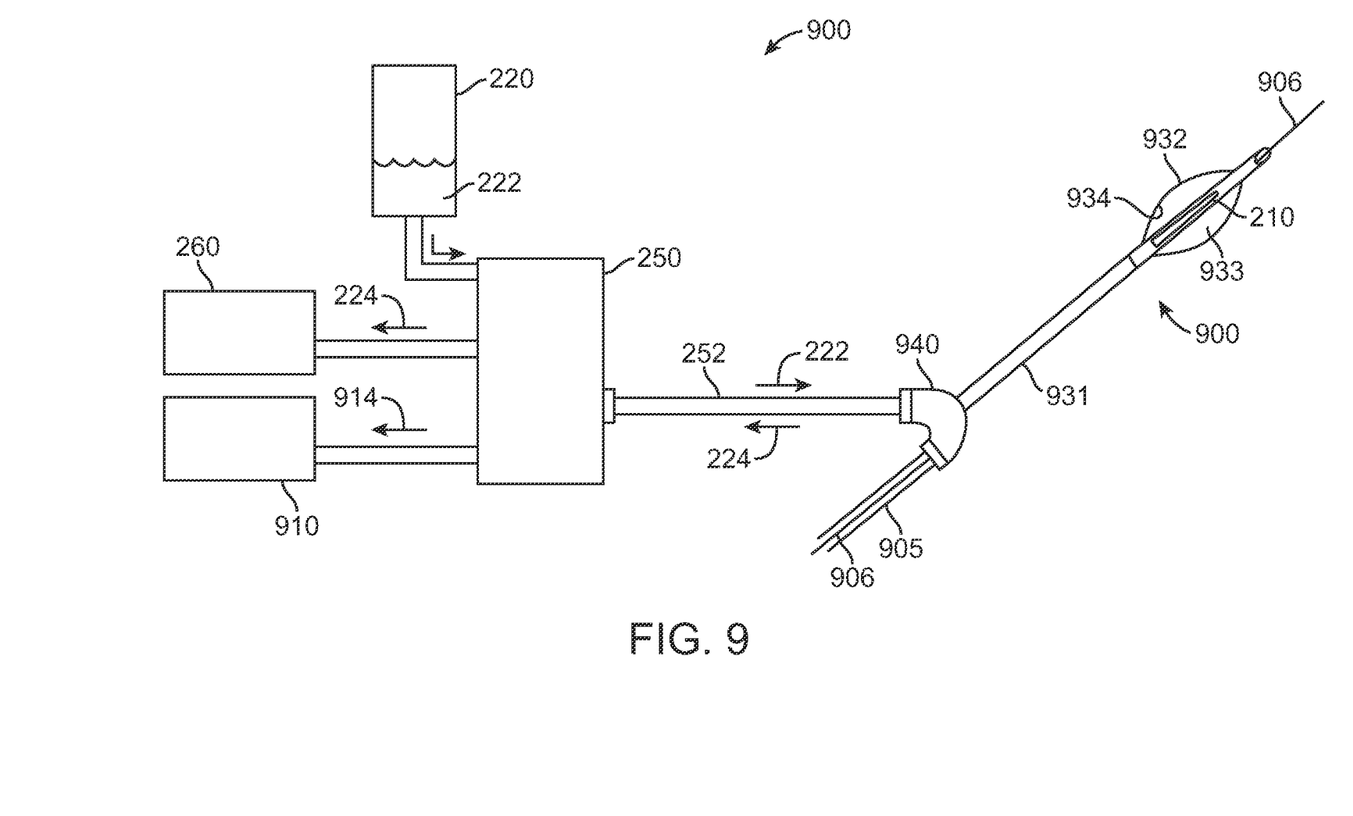
FIG. 9 schematically illustrates a cryo-ablation system constructed according to another embodiment and generally illustrates a tubular member having multiple coaxial tubes of different lengths for dispersing coolant within an inflatable element of a cyroablation balloon catheter.

Referring to FIG. 9, other embodiments involve the use of a cyroablation balloon catheter 900 that includes one or more inflatable element or balloons 932 (one balloon is illustrated in FIG. 9 for ease of illustration), the inner surface 934 of which defines an inner space or expansion chamber 933. In the illustrated system, a guide wire 906 can be advanced through a guide wire lumen 905 to maneuver and guide the catheter 900 to a desired location within a patient, e.g., within the patient's heart for treatment of atrial fibrillation. Further, a vacuum 910 may be provided to evacuate fluid 914 to control the vacuum level in a space between balloons.

Figure 10:
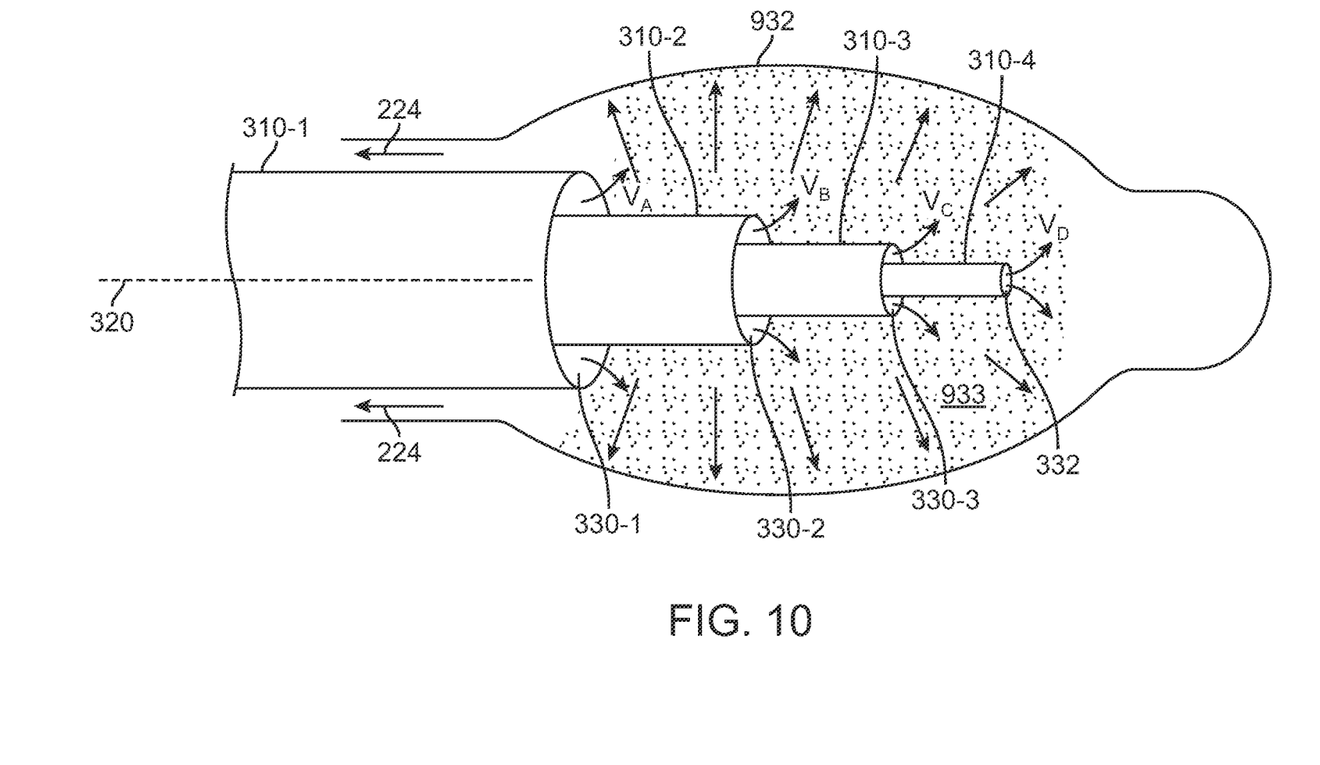
FIG. 10 illustrates a cryo-ablation device constructed according to one embodiment that includes an inflatable or expandable element of a cryogenic balloon catheter and a tubular member constructed according to one embodiment positioned within an inner space of the inflatable element.
Figure 11:
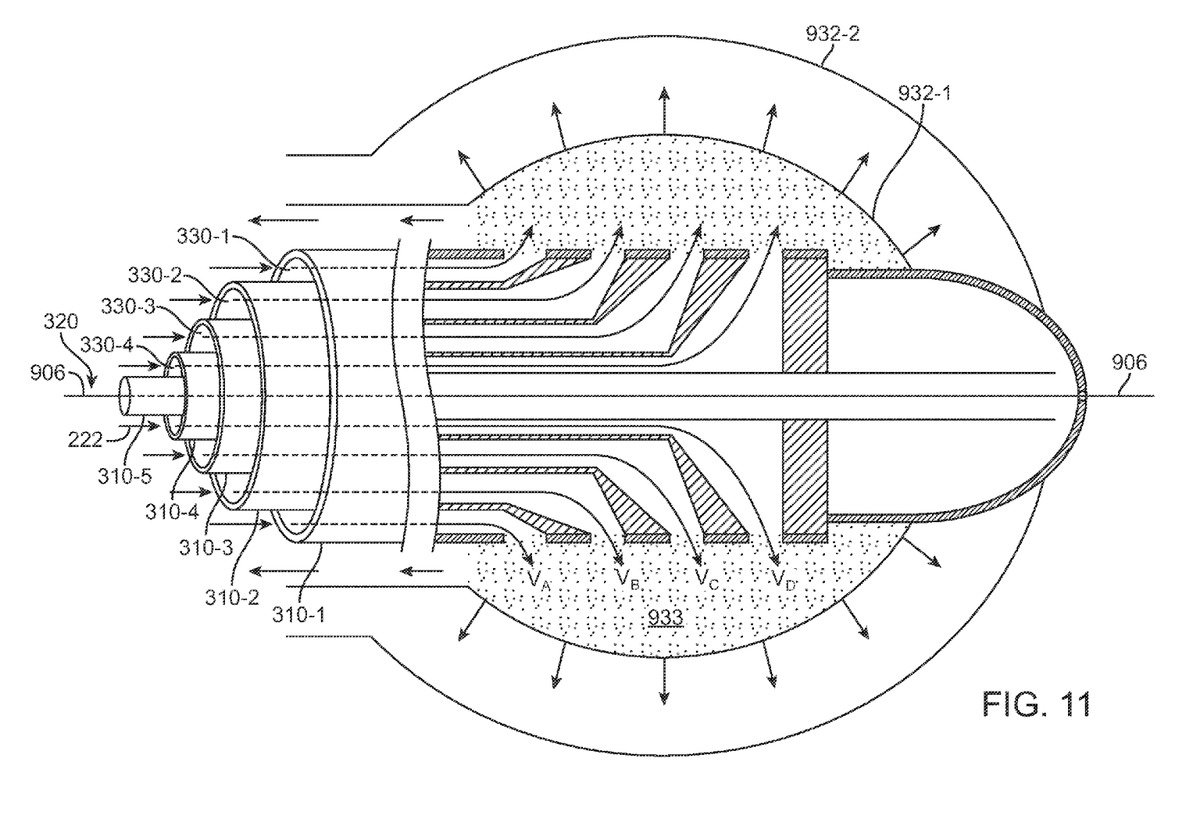
FIG. 11 illustrates another manner in which a tubular member constructed according to one embodiment may be integrated within a cryogenic balloon catheter.

FIG. 10 illustrates one example of how a tubular member 210, e.g., as shown in FIG. 5, may be incorporated into an inner space or expansion region 933 of a balloon 932. FIG. 10 illustrates one balloon 932, but a second or outer balloon may also be utilized. Tubular members 210 having other numbers of tubes 310 may also be utilized, e.g., as shown in FIGS. 3, 6, 7 and 11 (which also shows two balloons 932-1 and 932-2). As shown in FIG. 11, a tubular member or tubes 310 may be part of a balloon assembly that accommodates a guide wire 906. Tubes or extensions extending there from or dividers may be incorporated into the assembly to facilitate flow of coolant from the respective tubes 310 and into the space 933 defined by a balloon.

Figure 12:
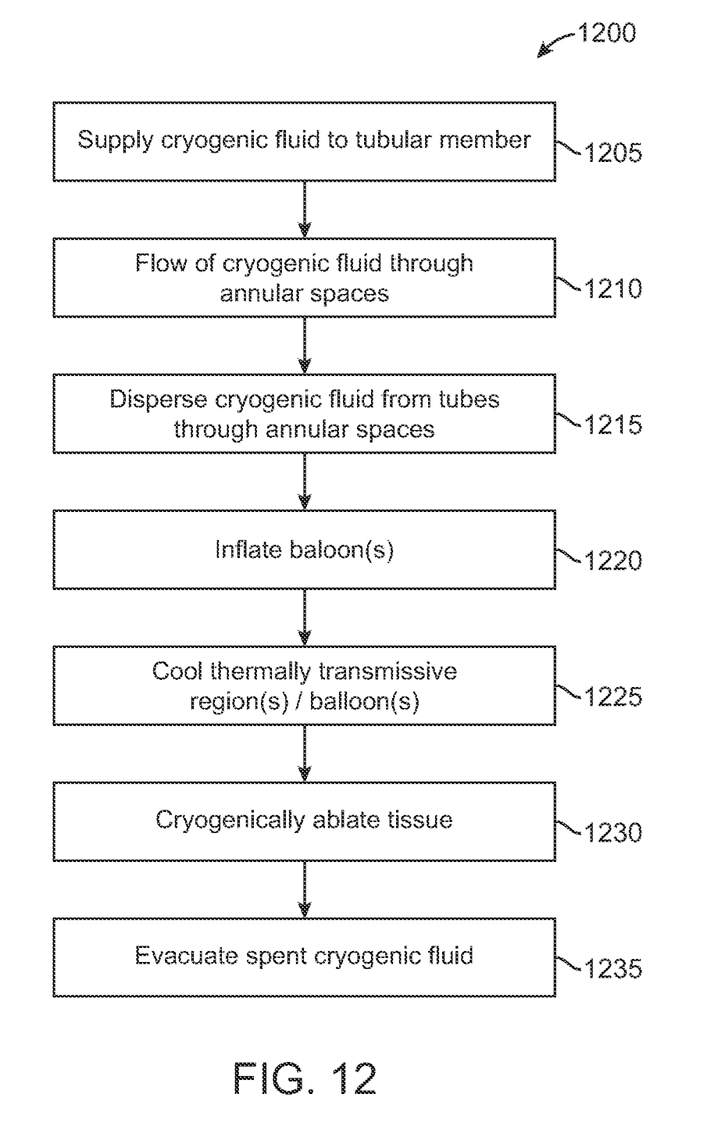
FIG. 12 is a flow diagram of a method for dispersing coolant within a cryogenic balloon catheter utilizing tubular member embodiments.

Referring to FIG. 12, a method 1200 for performing cryoablation with tubular member 210 embodiments incorporated into a balloon catheter 900 includes, at stage 1205, manipulating or positioning the balloon catheter 900 at a desired location within a patient. For example, this may be done utilizing the guide wire 906 or other component or control element.

At stage 1210, one or more valves can be manipulated to release coolant 222 and/or allow coolant 222 to flow through a console or interface 250 and associated connectors or tubes 252, through a handle 940 or other component and the catheter body 931, and to the tubular member 210 that is positioned within and in fluid communication with the inner space 933 of the balloon 932.

At stage 1215, the coolant 222 flows through different sections of the tubular member 210. For example, with the tubular member 210 illustrated in FIG. 3, coolant 222 can flow through the first and second annular spaces 330-1 and 330-2. In certain embodiments, as illustrated in FIG. 9, a central lumen may be utilized for a guide wire 906 rather than for dispersing coolant 222, but various structural configurations can be utilized. As discussed above, the annular spaces 330 may have different cross sectional areas such that the quantities or volumes of coolant 222 released from the tubes 310 at each axial location along the tubular member 210 may be approximately the same such that the coolant 222 is uniformly sprayed into and distributed within the inner space 933 of the balloon 932

At stage 1220, the coolant 222 flows through the annular spaces 330 and/or central lumen 332 and is released, dispersed or sprayed from the respective annular outlets and/or central lumen 332 defined by the respective tubes 310 at different axial locations along the tubular member 210, thereby inflating the balloon 932. According to one embodiment, the quantity of coolant 222 released at each axial location is approximately the same such that the coolant 222 can be uniformly or substantially uniformly distributed within the inner space 933 of the balloon 932 to uniformly or substantially uniformly chill the balloon 932 at stage 1225, and cryogenically ablate tissue that is adjacent to or that surrounds the chilled balloon 932 at stage 1230. With embodiments, tissue ablation 430 is uniform or substantially uniform as a result of the uniform or substantially uniform distribution of coolant 222 within the balloon 932. At stage 435, spent coolant 224 is evacuated from the balloon 900 through an exhaust path suing using associated vacuum tube 262 and vacuum source 260, which may be part of an open loop system, a close loop system or a scavenging system.

Figure 13:
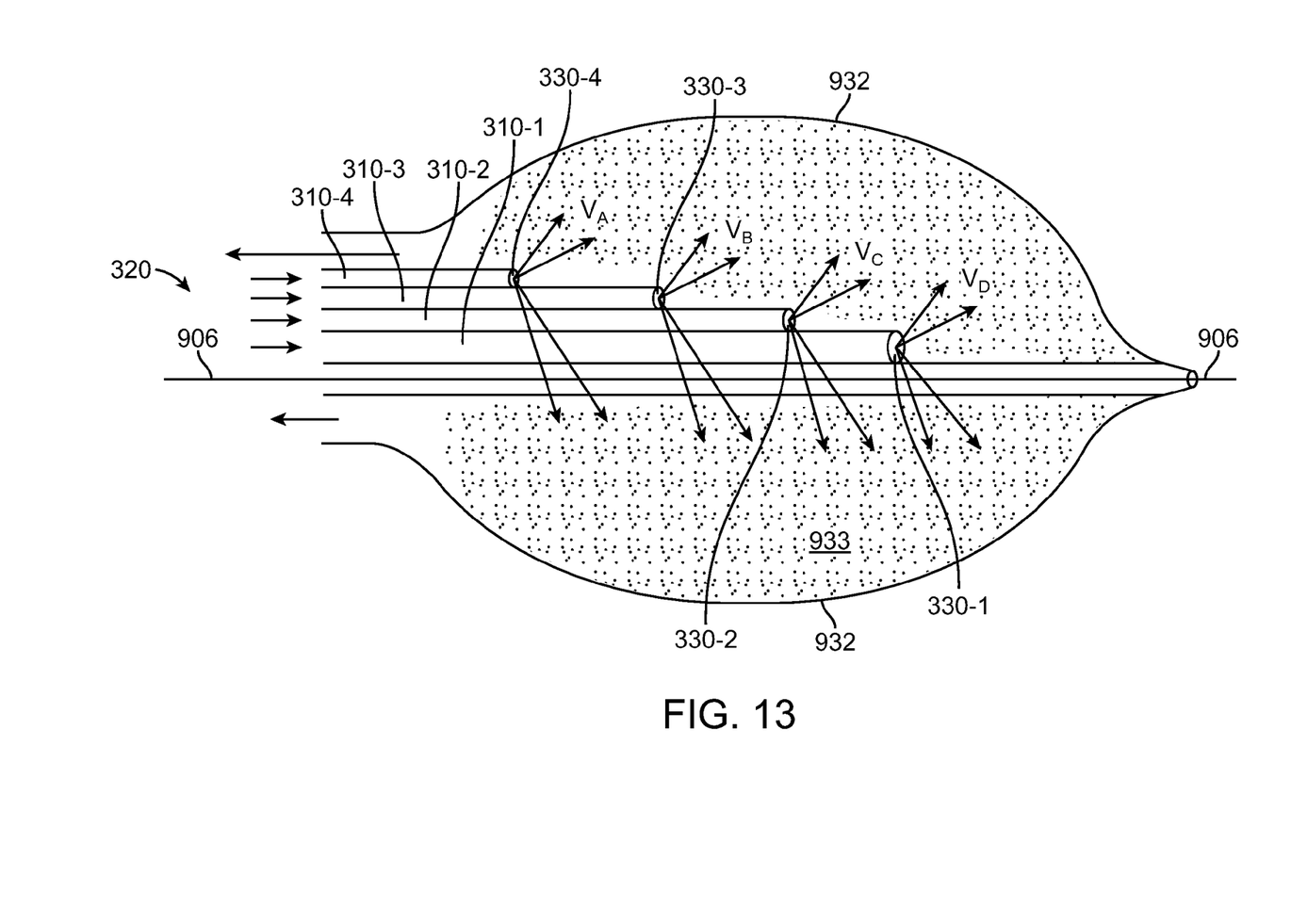
FIG. 13 illustrates a tubular member having multiple tubes arranged in a non-coaxial manner and integrated within a cryogenic balloon catheter to disperse coolant at different axial locations within a balloon.

Referring to FIG. 13, in another embodiment, a tubular member 210 having a non-coaxial arrangement of tubes (e.g., as shown in FIG. 8) may be incorporated into a cryo-ablation balloon catheter 900. In the illustrated embodiment, a tubular member 210 includes four tubes 310-1 to 310-4, having different diameters D1-D4 and that extend to different lengths or that terminate at different locations within the inner space 933 of a balloon 932. In this manner, the quantities or volumes (Va-Vd) of coolant 222 released from the tubes 310 at each axial location along the tubular member 210 being approximately the same (Va~Vb~Vc~Vd) such that the coolant 222 is uniformly sprayed into and distributed within the inner space 233 of the thermally transmissive region 232.

Although particular embodiments have been shown and described, it should be understood that the above discussion is not intended to limit the scope of these embodiments. Various changes and modifications may be made without departing from the scope of the claims.

For example, it should be understood that tubular member embodiments may involve various number of tubes and sizes thereof, and that the sizes of annular spaces and central lumens may vary, and that the dimensions provided are provided as examples of how embodiments may be implemented. Further, embodiments may be used in steerable and non-steerable device that may or may not include an inflatable element. Embodiments of components can also be made of various materials suitable for cryo-ablation applications. Further, embodiments may be configured to perform ablation of various types of tissue for treatment of different conditions or diseases, one example of which is to perform endocardial ablation to treat atrial fibrillation as described above. Thus, embodiments are intended to cover alternatives, modifications, and equivalents that may fall within the scope of the claims.

What is claimed is:

1. An apparatus for dispersing a coolant within a cryoablation device positionable within a patient, comprising:
a tubular member configured for insertion within a body of the cryo-ablation device, the tubular member comprising a plurality of coaxial tubes having different diameters and extending to different lengths within the cryo-ablation device body, the plurality of coaxial tubes defining a respective plurality of annular spaces such that coolant can flow through the plurality of annular spaces and be released from only a distal terminus of a distal portion of each of the plurality of tubes at different axial locations along the tubular member, the plurality of coaxial tubes comprising at least an outer tube and an inner tube disposed at least partially within the outer tube, the inner tube defining a central lumen through which coolant is released, wherein a distal end of the inner tube extends distally beyond a distal end of the outer tube.

2. The apparatus of claim 1, the plurality of coaxial tubes being arranged in a telescoping configuration.

3. The apparatus of claim 1, the tubular member being configured such that substantially a same quantity of coolant is released at each of the different axial locations.

4. The apparatus of claim 1, the plurality of coaxial tubes defining respective annular spaces having different cross-sectional areas.

5. The apparatus of claim 4, wherein cross-sectional areas of the respective annular spaces increase along a length of the tubular member towards a distal end of the tubular member.

6. The apparatus of claim 1, the plurality of coaxial tubes each having a substantially same shape.

7. The apparatus of claim 1, the axial locations being substantially equally spaced apart from one another.

8. An apparatus for dispersing a coolant within a cryo-ablation device positionable within a patient, comprising:
 a tubular member configured for insertion within a body of the cryo-ablation device, the tubular member comprising a plurality of coaxial tubes having different diameters and extending to different lengths within the cryo-ablation device body, the plurality of coaxial tubes defining a respective plurality of annular spaces such that coolant can flow through the plurality of annular spaces and be released from the plurality of tubes at different axial locations along the tubular member;
 wherein the plurality of coaxial tubes includes
  a first tube,
  a second tube coaxially disposed within the first tube and extending beyond a distal end of the first tube, and
  a third tube coaxially disposed within the second tube and extending beyond a distal end of the second tube,
  a first annular space being defined between an inner surface of the first tube and an outer surface of the second tube, a second annular space being defined between an inner surface of the second tube and an outer surface of the third tube, wherein coolant can flow through the first and second annular spaces and a central lumen defined by the third tube to be released from respective tubes at different axial locations along the tubular member.

9. The apparatus of claim 8, the tubular member being configured such that a quantity of coolant released at each axial location is approximately the same.

10. The apparatus of claim 8, each annular space having a different cross-sectional area.

11. The apparatus of claim 8, a cross-sectional area of each annular space being less than a cross-sectional area of the central lumen.

12. A cryo-ablation apparatus, comprising:
 a body configured for insertion into a patent, the body comprising a thermally transmissive region having an inner surface and an outer surface and defining an inner space in which a coolant can flow; and
 a tubular member positioned within the thermally transmissive region, the tubular member comprising a plurality of coaxial tubes having different diameters and extending to different lengths within the inner space to define a plurality of annular spaces, wherein coolant can flow through the annular spaces and be dispersed from only a distal terminus of a distal portion of each of the plurality of tubes at different axial locations along the tubular member and into the inner space of the thermally transmissive region, the plurality of coaxial tubes comprising at least an outer tube and an inner tube disposed at least partially within the outer tube, the inner tube defining a central lumen through which coolant is released, wherein a distal end of the inner tube extends distally beyond a distal end of the outer tube.

13. The apparatus of claim 12, the plurality of coaxial tubes being arranged in a telescoping configuration.

14. The apparatus of claim 12, the tubular member being configured such that a quantity of coolant released at each axial location is approximately the same.

15. The apparatus of claim 12, wherein distal ends of the inner and outer tubes are disposed within the inner space of the thermally transmissive region.

16. The apparatus of claim 12, the plurality of coaxial tubes defining annular spaces having different cross-sectional areas.

17. The apparatus of claim 16, the cross-sectional areas of annular spaces increasing along a length of the tubular member towards a distal end of the tubular member.

18. The apparatus of claim 12, the plurality of coaxial tubes being the same shape, and the axial locations being equally spaced apart from each other.

* * * * *